US008012907B2

(12) United States Patent
Berrada

(10) Patent No.: US 8,012,907 B2
(45) Date of Patent: Sep. 6, 2011

(54) GUANIDINATED POLYSACCHARIDES, THEIR USE AS ABSORBENTS AND PROCESS FOR PRODUCING SAME

(75) Inventor: Mohammed Berrada, Longueuil (CA)

(73) Assignee: Archer Daniels Midland Company, Decatur, IL (US)

( * ) Notice: Subject to any disclaimer, the term of this patent is extended or adjusted under 35 U.S.C. 154(b) by 531 days.

(21) Appl. No.: 11/575,018

(22) PCT Filed: Sep. 14, 2005

(86) PCT No.: PCT/CA2005/001399
§ 371 (c)(1),
(2), (4) Date: Jul. 28, 2008

(87) PCT Pub. No.: WO2006/029519
PCT Pub. Date: Mar. 23, 2006

(65) Prior Publication Data
US 2008/0305950 A1    Dec. 11, 2008

(51) Int. Cl.
*B01J 20/26* (2006.01)
(52) U.S. Cl. ......... 502/402; 502/404; 536/55.1; 536/30; 530/300
(58) Field of Classification Search .............. 502/402, 502/404; 536/55.1, 30; 530/300
See application file for complete search history.

(56) References Cited

U.S. PATENT DOCUMENTS

| | | | |
|---|---|---|---|
| 2,131,120 A | 9/1938 | Schlack | 8/189 |
| 3,230,213 A | 1/1966 | Mehltretter | 536/45 |
| 3,422,087 A | 1/1969 | Caesar | 536/20 |
| 3,856,715 A | 12/1974 | Corte et al. | 521/30 |
| 4,281,109 A | 7/1981 | Jarowenko et al. | 536/50 |
| 4,464,528 A | 8/1984 | Tasset | 536/50 |
| 4,505,775 A | 3/1985 | Harding et al. | 162/9 |
| 5,470,964 A | 11/1995 | Qin | 536/20 |
| 5,498,705 A | 3/1996 | Oin | 536/20 |
| 5,550,189 A | 8/1996 | Qin et al. | 525/54.3 |
| 5,637,681 A | 6/1997 | Stockel | 536/20 |
| 5,718,770 A | 2/1998 | Shah et al. | 127/65 |
| 5,780,616 A | 7/1998 | Fornasari et al. | 536/30 |
| 5,888,988 A * | 3/1999 | Elson | 514/55 |
| 5,932,017 A | 8/1999 | Chiu et al. | 127/67 |
| 6,087,448 A | 7/2000 | Mitchell et al. | 525/217 |
| 6,159,721 A | 12/2000 | Cheng et al. | 435/219 |
| 6,231,675 B1 | 5/2001 | Chiu et al. | 127/67 |
| 6,277,186 B1 | 8/2001 | Shi et al. | 106/205.72 |
| 6,294,163 B1 | 9/2001 | Dhal et al. | 424/78.01 |
| 6,451,121 B2 | 9/2002 | Chiu et al. | 127/29 |
| 2003/0177534 A1 | 9/2003 | Nichols et al. | 800/284 |
| 2003/0232965 A1 * | 12/2003 | Bergeron | 530/300 |
| 2004/0229265 A1 | 11/2004 | Lapidot et al. | 435/6 |
| 2004/0244706 A1 | 12/2004 | Kurauchi et al. | 119/161 |
| 2004/0265435 A1 | 12/2004 | Kurauchi et al. | 426/106 |
| 2007/0068824 A1 * | 3/2007 | Payne et al. | 205/317 |

FOREIGN PATENT DOCUMENTS

| | | |
|---|---|---|
| CA | 2308537 | 11/2000 |
| CA | 2362006 | 5/2002 |
| CA | 2426478 | 10/2003 |
| CA | 2462053 | 9/2004 |
| CA | 2483049 | 3/2005 |
| EP | 1405559 | 4/2004 |
| JP | 59-102939 | 6/1984 |
| JP | 60-233102 | 11/1985 |
| WO | WO 98/50050 | 11/1998 |
| WO | WO 99/29352 | 6/1999 |
| WO | WO 00/35504 | 6/2000 |
| WO | WO 00/39139 | 7/2000 |
| WO | WO 01/34656 | 5/2001 |
| WO | WO 03/090801 | 11/2003 |
| WO | WO 2004/073034 | 8/2004 |

OTHER PUBLICATIONS

Masic et al., "Arginine mimetics," *Tetrahedron*, 57:7073-7105, 2001.
Buchholz and Graham, In: *Modern superabsorbent polymer technology*, Ed. Wiley-VCH, New York, 1998.
Riccardo, "Water-absorbent polymers: a patent survey," *Rev. Macromol. Chem. Phys.*, C 34:607-662, 1994.
Tijsen et al., "An experimental study on the carboxymethylation of granular potato starch in non-aqueous media," *Carbohydr. Polym.*, 45:219-226, 2001.

* cited by examiner

*Primary Examiner* — Melvin C Mayes
*Assistant Examiner* — Melissa Stalder

(57) ABSTRACT

The present invention relates to cationic, gel forming, guanidinated polysaccharides of Formula I, their use as absorbent materials, and to processes for producing same: Formula I wherein $Z_1$, $Z_2$, and $Z_3$ are independently selected from the group consisting of hydrogen, $C_1$-$C_{10}$ alkyl, substituted $C_1$-$C_{10}$ alkyl, $C_5$-$C_7$ cycloalkyl, and benzyl; and m is an integer ranging from 1 to 2,000,000. The absorbent guanidinated polysaccharides of Formula I have absorbent properties suitable for use in personal care products.

39 Claims, No Drawings

GUANIDINATED POLYSACCHARIDES, THEIR USE AS ABSORBENTS AND PROCESS FOR PRODUCING SAME

CROSS REFERENCE TO RELATED APPLICATIONS

The present application is a national phase application under 35 U.S.C. §371 of International Application No. PCT/CA2005/001399, filed 14 Sep. 2005, which claims the benefit of Canadian Application No. 2,481,491 filed 14 Sep. 2004. The entire text of these applications are incorporated by reference.

FIELD OF THE INVENTION

The present invention relates to guanidinated polysaccharides, their use as absorbent materials, and to a process for producing same.

BACKGROUND OF THE INVENTION

Cationic polysaccharides constitute a very useful class of polymers. They are commonly used in a wide variety of industrial applications including papermaking and printing processes, cosmetics, personal care formulations, water treatment, oil drilling fluids, ore treatments, drug delivery systems, detergents, and textiles. They are particularly useful in the chemical field where they are commonly used as complexing agents to bind to negatively charged species, i.e. negatively charged particles or molecules.

Quaternary ammonium derivatized polysaccharides, such as the quaternary ammonium derivatives of guar, starch and cellulose, represent a commonly used family of cationic polysaccharides. These polysaccharides are usually prepared by reacting a polysaccharide with a quaternary amine derivative under alkaline conditions. Typical non-limitative examples of procedures for making cationic polysaccharides are disclosed by Tassett (U.S. Pat. No. 4,464,528), Jarowenko et al. (U.S. Pat. No. 4,281,109), Harding et al. (U.S. Pat. No. 4,505,775), Caesar (U.S. Pat. No. 3,422,087) and Schlack (U.S. Pat. No. 2,131,120).

Guanidine groups constitute strong bases, exhibiting pKa values often exceeding 12. These high pKa values can be attributed to π-electron delocalization of the characteristic C=N linkage (several resonance structures are possible for guanidine groups).

Guanidinium and/or bi-guanidinium groups have been grafted to chitosan as disclosed by Toshio (JP 60-233102), Stockel (U.S. Pat. No. 5,637,681) and Seo et al. (Kobunshi Robunshu, 53 (1), 1996, P 70-76). The amidation and guanidination reactions commonly involve the use of a cyanamide derivative. However, as reported by Elizer et al., polysaccharides comprising O-amidine linkages are unstable. Due the labile nature of the O-amidine linkage, these polysaccharides typically display a shelf-life of only about 24 hours at room temperature, and about 2 days at 0° C.

Payne et al. (WO 04/073034) teach that polysaccharides bearing guanidinium groups are particularly useful for electrochemical deposition on anodes. However, Payne et al. do not teach the absorbent properties of such guanidinated polysaccharides.

Polysaccharides comprising grafted guanylhydrazone groups have been disclosed by Mehltretter (U.S. Pat. No. 3,230,213) and Shima (JP 59-102939). The guanylhydrazone grafted polysaccharides were reported by Shima as possessing absorbent properties. The guanylhydrazone groups were grafted to the polysaccharide by reacting a periodate-oxidized starch with an aminoguanidine derivative. However, due to the inherent unstable nature of imines in aqueous and alkaline environments, guanylhydrazone grafted polysaccharides are not suited as absorbents for liquids.

Arginine modified polysaccharides have been disclosed by Cheng et al. (U.S. Pat. No. 6,159,721), Kurauchi et al. (US 2004/0244706 A1; US 2004/0265435 A1) and Lapidot et al. (US 2004/0229265; WO 00/39139 A1). More specifically, an L-arginine-modified pectin has been disclosed by Cheng et al. However, the enzyme catalyzed amidation reaction is specific to water-soluble polymers having alkoxy and carboxylic acid functionalities, e.g. pectin. An amino-acid ester of cellulose was described by Kurauchi et al. However, Kurauchi et al. do not teach the ester as forming gels, an essential property of absorbent materials for trapping liquids. The polysaccharides as reported by Lapidot et al., were not disclosed as being useful as absorbent materials.

Cationic polysaccharides having superabsorbent properties have been disclosed by Fornasari et al. (U.S. Pat. No. 5,780,616). These polysaccharides, having a degree of substitution (DS) of at least 0.5, are substituted by quaternary ammonium groups, and are cross-linked to a sufficient extent such that they remain insoluble in water. An increase in the number of functional groups in the product was reported as improving the superabsorbent properties.

Resins comprising guanidine groups have found wide spread use as strongly basic anion exchange resins, and have been disclosed by Corte et al., (U.S. Pat. No. 3,856,715) and Matie et al., (Omagiu Raluca Ripan pp. 363-374, 1966). Furthermore, poly(vinylguanidine)-based superabsorbent gels have been disclosed by Mitchell et al. (U.S. Pat. No. 6,087,448). However, this material was not reported as being biodegradable.

Water absorbent materials, such as superabsorbent polymers, can be employed in various applications such as in disposable sanitary products (e.g. diapers, incontinence articles, feminine hygiene products, airlaids and absorbent dressings), household articles, sealing materials, humectants in agricultural products for soil conditioning, anti-condensation coatings, water-storing materials in agriculture/horticulture, and as chemical absorbents. Furthermore, they can be employed in applications related to the transportation of fresh food or seafood, and in food packaging applications.

Superabsorbent polymers can be grouped into the following categories: i) naturally occurring polymers (e.g. starch and other physically modified polysaccharides); ii) semi-synthetic polymers (e.g. carboxyalkylated starch and crosslinked derivatives); and iii) synthetic polymers.

Synthetic water absorbent polymers have experienced rapid development, resulting in diversities and quantities far exceeding those observed for natural and semi-synthetic water absorbent polymers.

Polyacrylates, polyacrylamides, and their copolymers are among the best known synthetic superabsorbent polymers. Acrylic superabsorbent polymers are described in "*Modern Superabsorbent Polymer Technology*", Buchholz F. L. and Graham A. T. Eds., Wiley-VCH, New York, 1998.

Crosslinked polyacrylic acids (and corresponding salts) have hitherto been used as water absorbent materials. However, crosslinked polyacrylic acids (and corresponding salts) do not easily biodegrade. Moreover, cross-linked polyacrylic acids are obtained from non-renewable feedstocks, creating provisioning problems.

Semi-synthetic superabsorbent polysaccharide-based grafted polymers are obtained through grafting of an unsaturated monomer (acrylonitrile, acrylic acid, acrylamide) onto starch or, less frequently, cellulose. Such polymers, also called "Super Slurpers", have shown water absorption ranging from 700 to 5300 g/g for deionized water, and up to 140 g/g in a 0.9% saline solution (weight by weight of NaCl, referred to hereinafter as saline solution) (Ricardo P. O., *Water-Absorbent Polymers: A Patent Survey*. J. Macromol. Sci., Rev. Macromol. Chem. Phys., 1994, 607-662 (p. 634). Despite their high water absorption, these grafted polysaccharides, prepared by radical polymerization, are known for not being biodegradable and hypoallergenic.

There is a growing interest in the exploitation of natural polymers for commercial applications. Ideally, these natural polymers are derived from renewable sources (e.g. chitin, starch, guar or cellulose), providing for environmentally friendly products. There is a particular interest in chitin, a natural polymer extracted from crustacean shells such as crabs, lobsters, shrimps and insects. It is considered the second most abundant polysaccharide on earth, after cellulose. Chitosan, which is derived from chitin by deacetylation, is structurally similar to cellulose.

Modified starches have also been used as biodegradable absorbent materials as disclosed by Qin et al. (U.S. Pat. Nos. 5,550,189; 5,498,705; and 5,470,964), Besemer et al. (WO 0035504A1; WO 0134656A1; and WO 9929352A1), Chung-Wai et al. (U.S. Pat. Nos. 5,932,017; 6,231,675; and 6,451,121), Shah et al. (U.S. Pat. No. 5,718,770), (Shi et al. U.S. Pat. No. 6,277,186) as well as by Beenackers A. A. C. M. et al. (Carbohydr. Polym., 2001, 45, 219-226). Oligomeric polyethylene glycol crosslinked polysaccharides, in particular polyethylene glycol crosslinked starch, have also been disclosed as useful absorbents by Couture et al. (CA 2,362,006).

The use of biodegradable, glass-like, pregelatinized starch as an absorbent for liquids has been previously disclosed by Huppe et al. (CA 2,308,537). However, this pregelatinized starch was shown to only absorb 8 g/g, which is insufficient to be useful for use in the hygiene industry. In order to improve the absorption capacities of this modified starch, it was mixed with xanthan and guar gums. Moreover, it has also been mixed with sodium carboxymethyl cellulose (CMC). However, the absorption performances remained insufficient to be useful for use in applications requiring a high degree of absorption, such as in baby diapers. The absorption characteristics of this modified starch could be attributed to amylopectin, a high molecular weight polysaccharide component of starch. It was found that amylopectin, when crosslinked, provides for materials having improved absorption characteristics [Thibodeau et al. (CA 2,462,053)]. Furthermore, as disclosed by Bergeron et al. (CA 2,426,478), it was observed that these modified starches could synergistically interact with mannose containing polysaccharides, ionic polysaccharides, gelling proteins or mixtures thereof. These synergistic interactions have been found to be especially useful in formulating absorbent materials. More recently, Berrada et al. (CA 2,483,049) disclosed that phylosilicates, when dispersed in an absorbent polysaccharide matrix, generate a nanocomposite system having excellent absorbent characteristics.

Unfortunately, most modified polysaccharide-based materials do not possess absorptive properties comparable to many of the synthetic, highly-absorptive materials. Moreover, most polysaccharide based materials are based on anionic or neutral polysaccharides, preventing their use in multivalent cationic environments such as drilling fluids and physiological fluids. This in turn has prevented acceptance and widespread use of such modified polysaccharides in absorbent personal care products.

There thus remains a need for modified highly absorbent natural-based polysaccharides suitable for use in personal care products.

The present invention seeks to meet these and other needs.

The present invention refers to a number of documents, the content of which is herein incorporated by reference in their entirety.

SUMMARY OF THE INVENTION

The present invention broadly relates to modified, highly absorbent natural-based polysaccharides, suitable for use in personal care products. In an embodiment, the present invention relates to cationic, gel forming, guanidinated polysaccharides, and salts thereof, having absorbent properties suitable for use in personal care absorbent products.

In a further embodiment, the guanidinated polysaccharides are based on polysaccharides obtained from natural, renewable and biodegradable sources.

In a further embodiment, the present invention relates to a guanidinated polysaccharide of Formula I:

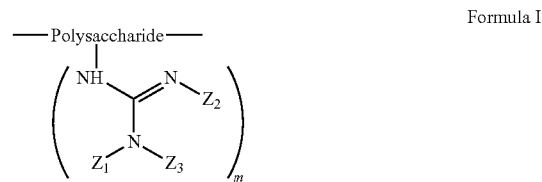

Formula I wherein:

$Z_1$, $Z_2$ and $Z_3$ are independently selected from the group consisting of hydrogen, $C_1$-$C_{10}$ alkyl, substituted $C_1$-$C_{10}$ alkyl, $C_5$-$C_7$ cycloalkyl, and benzyl, and wherein the substituents are selected from the group consisting of $C_1$-$C_5$ alkyl, and amino groups; and m is an integer of at least 1, more preferably an integer ranging from 20 to 2,000,000.

In a further embodiment, the present invention relates to a process for making guanidinated polysaccharides, and salts thereof, useful as absorbent materials.

In yet a further embodiment, the present invention relates to a process for making guanidinated polysaccharides, the process comprising reacting an aminated polysaccharide of Formula II:

Polysaccharide-NH₂   Formula II with a compound of Formula III:

Formula III wherein:

$Z_1$, $Z_2$ and $Z_3$ are independently selected from the group consisting of hydrogen, $C_1$-$C_{10}$ alkyl, substituted $C_1$-$C_{10}$ alkyl, $C_5$-$C_7$ cycloalkyl, and benzyl, and wherein the substituents are selected from the group consisting of $C_1$-$C_5$ alkyl, and amino groups; and LG is a leaving group selected from the group consisting of pyrazoles, chlorides, bromides, iodides, cyanides, azides, thiocyanates, tosylates, mesylates, triflates, picrates, nosylates and brosylates.

In yet a further embodiment, the present invention relates to a process for making guanidinated polysaccharides, the process comprising reacting an aminated polysaccharide of Formula II:

Polysaccharide-NH$_2$        Formula II with a compound of Formula IV:

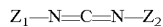
$Z_1$—N=C=N—$Z_2$        Formula IV wherein:

$Z_1$, and $Z_2$ are independently selected from the group consisting of hydrogen, $C_1$-$C_{10}$ alkyl, substituted $C_1$-$C_{10}$ alkyl, $C_5$-$C_7$ cycloalkyl, and benzyl, and wherein the substituents are selected from the group consisting of $C_1$-$C_5$ alkyl, and amino groups.

In yet a further embodiment, the present invention relates to absorbent compositions comprising at least one cationic guanidinated polysaccharide or a salt thereof and a co-absorbent. Non-limitative examples of co-absorbents include fibers as well as natural, semi-synthetic or synthetic absorbent materials.

In yet a further embodiment, the present invention relates to the use of cationic guanidinated polysaccharides, and/or compositions thereof as superabsorbents in personal hygiene products including baby diapers, incontinence products, and sanitary napkins as well as in other applications such as in the pulp and paper industry (i.e. absorbent paper products), in the textile industry, in printing applications, in ore treatments, in pet litter, in water treatment, in food pads (i.e. applications related to the transportation of fresh food and food packaging), in detergents, in oil drilling fluids (i.e. as lost circulation material), in agricultural and forestry applications for retaining water in the soil and for the release of water to the roots of plants and trees, in fire-fighting gels, in sealing materials, in anti-condensation coatings, in bandages and surgical pads (i.e. wound dressings), for the cleanup of acidic and/or basic aqueous spills including water soluble chemical spills, as polymeric gels for the slow and controlled release of cosmetics and pharmaceuticals (also known as drug delivery systems), as airlaids, and finally in the manufacture of artificial snow.

In yet a further embodiment, the present invention relates to the use of cationic guanidinated polysaccharides, salts, and/or compositions thereof as superabsorbents for liquids, non-limitative examples of which include water, aqueous solutions, physiological fluids and saline solutions.

In yet a further embodiment, the present invention relates to gels of cationic guanidinated polysaccharides as well as to particles of such cationic guanidinated polysaccharides.

Finally, the present invention relates to the use of cationic guanidinated polysaccharides and/or compositions thereof as water-swellable, water-insoluble superabsorbents.

Other objects, features and advantages of the present invention will become more apparent upon reading of the following non-restrictive description of illustrative embodiments, which is exemplary and should not be interpreted as limiting the scope of the present invention.

DETAILED DESCRIPTION OF ILLUSTRATIVE EMBODIMENTS

In order to provide a clear and consistent understanding of the terms used in the present specification, a number of definitions are provided below. Moreover, the present description refers to a number of routinely used chemical terms; definitions of selected terms are provided for clarity and consistency.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or method steps.

The term "about" is used to indicate that a value includes an inherent variation of error for the device or the method being employed to determine the value.

It is contemplated that any embodiment discussed in this specification can be implemented with respect to any method or composition of the invention, and vice versa. Furthermore, compositions of the invention can be used to achieve methods of the invention.

As used herein, the term "Free Swell Capacity" (FSC), also called "Total Absorption" refers to the amount (g) of fluid absorbed per gram of the composition. Typical fluids are blood, synthetic blood and saline solutions (0.9% Weight/Weight NaCl solution, hereinafter called 0.9% NaCl solution or saline).

As used herein, the term "Centrifuge Retention Capacity" (CRC) also called "Retention", refers to the amount (g) of fluid retained per gram of the composition, following exposure of the composition to a centrifugation force of 250 G. Typical fluids are blood, synthetic blood and saline solutions (0.9% Weight/Weight NaCl solution, hereinafter called 0.9% NaCl solution or saline).

As used herein, the term "Absorption Under Load" (AUL) at 0.3 PSI, 0.7 PSI or 0.9 PSI, also called "Absorption Against Pressure", refers to the amount (g) of fluid absorbed per gram of the composition. Typical fluids are blood, synthetic blood and saline solutions (0.9% Weight/Weight NaCl solution, hereinafter called 0.9% NaCl solution or saline).

As used herein, the term "absorbent" refers to materials forming a hydrogel upon contact with fluids, trapping fluids within the hydrogel.

As used herein, the term "superabsorbent" refers to absorbent materials characterized by a free swell capacity of at least 15 g/g.

As used herein, the term "polysaccharide" refers to polymers comprising a backbone consisting mainly (at least about 90%) of monosaccharide repeating units and/or derivatized monosaccharide repeating units. Non-limitative examples of polysaccharides include starches, modified starches, amylopectin, modified amylopectin, amylose, modified amylose, chitosan, chitin, guar gum, modified guar gum, locust bean gum, tara gum, konjac gum, konjac flour, fenugreek gum, mesquite gum, aloe mannans, cellulose, modified cellulose such as carboxyalkylated cellulose and carboxymethyl cellulose, oxidized polysaccharides, sulfated polysaccharides, cationic polysaccharides, pectin, arabic gum, karaya gum, xanthan, kappa, iota or lambda carrageenans, agar-agar and alginates. Non-limitative examples of mannose-based polysaccharides include guar gum, tara gum, locust bean gum, konjac, mesquite gum, and fenugreek extracts.

As used herein, the term "aminated polysaccharide" refers to polysaccharides bearing amino groups (—NH— or —NH$_2$), as well as genetically modified amino-bearing polysaccharides such as those described by Nichols et al. (US 2003/0177534 A1). The amino groups can be naturally occurring on the polysaccharide, such as on chitosan. The amino groups can also be artificially grafted to the polysaccharide, such as by alkylation or esterification procedures (e.g. alkylated and esterified polysaccharides). Non-limitative examples of such procedures are disclosed by Tassett (U.S. Pat. No. 4,464,528), Jarowenko et al. (U.S. Pat. No. 4,281,109), Harding et al. (U.S. Pat. No. 4,505,775), Caesar (U.S. Pat. No. 3,422,087) and Schlack (U.S. Pat. No. 2,131,120). Aminated polysaccharides comprise a wide range of amino groups (—NH— or —NH$_2$) grafted to the monosaccharide repeating units making up the polysaccharide.

As used herein, the term "guanidine moiety" includes guanidine, guanidinium, as well as guanidine derivatives such as (—NHC(NZ$_2$)NZ$_1$Z$_3$) wherein Z$_1$, Z$_2$ and Z$_3$ are as defined herein.

As used herein, the term "guanidinium" refers to the conjugate acid of guanidine; an ionically charged, cationic, species.

As used herein, the term "guanidinated polysaccharide" refers to polysaccharides bearing one or more guanidine groups or guanidinium groups. Guanidine and/or guanidinium bearing polysaccharides as contemplated by the present invention can be represented by the following generic structure of Formula I:

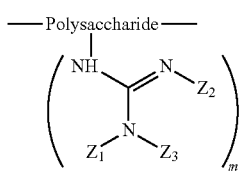

Formula I wherein Z$_1$, Z$_2$ and Z$_3$ are independently selected from the group consisting of hydrogen, C$_1$-C$_{10}$ alkyl, substituted C$_1$-C$_{10}$ alkyl, C$_5$-C$_7$ cycloalkyl, and benzyl, wherein the substituents are selected from the group consisting of C$_1$-C$_5$ alkyl and amino groups; and wherein m is an integer of at least 1, more preferably an integer ranging from 20 to 2,000,000.

As used herein, the term "C$_1$-C$_{10}$ alkyl" refers to hydrocarbon groups having 1 to 10 carbon atoms. Exemplary C$_1$-C$_{10}$ alkyl groups include methyl, ethyl, propyl, isopropyl, butyl, pentyl, hexyl, heptyl, octyl, nonyl and decyl.

As used herein, the term "substituted C$_1$-C$_{10}$ alkyl" refers to hydrocarbon groups having 1 to 10 carbon atoms as defined herein above, optionally substituted with a substituent selected from the group consisting of C$_1$-C$_5$ alkyl and amino groups. Exemplary C$_1$-C$_5$ alkyl groups include methyl, ethyl, propyl, isopropyl, isobutyl, n-butyl, t-butyl and pentyl.

As used herein, the term "C$_5$-C$_7$ cycloalkyl" refers to cyclic hydrocarbon groups having 5 to 7 carbon atoms. Exemplary C$_5$-C$_7$ cycloalkyl groups include cyclopentyl, cyclohexyl and cycloheptyl.

As used herein, the term "amidine" refers to groups represented by the following generic structure:

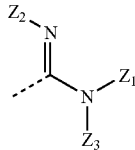

wherein Z$_1$, Z$_2$ and Z$_3$ are independently selected from the group consisting of hydrogen, C$_1$-C$_{10}$ alkyl, substituted C$_1$-C$_{10}$ alkyl, C$_5$-C$_7$ cycloalkyl, and benzyl, wherein the substituents are selected from the group consisting of C$_1$-C$_5$ alkyl and amino groups. Amidine groups, as described hereinabove, are grafted to the amine comprising polysaccharides, forming the desired guanidinated polysaccharides.

As used herein, the term "substituted" refers to the number of amidine groups grafted to the aminated polysaccharide, generating the desired guanidine groups. The number of amidine groups to be grafted to the aminated polysaccharide is at least 1. In an embodiment of the present invention, the number of amidine groups to be grafted to the aminated polysaccharide ranges from about 20 to about 2,000,000.

As used herein, the term "monosaccharide unit", refers to cyclic C$_5$-C$_6$ aldoses or ketoses. Non limitative examples of C$_5$-C$_6$ aldoses include allose, altrose, glucose, mannose, gulose, idose, galactose, talose, ribose, arabinose, xylose, lyxose. Non limitative examples of C$_5$-C$_6$ ketoses include ribulose, xylulose, fructose, sorbose and tagatose.

As used herein, the term "monosaccharide derivatives" refers to any chemically or enzymatically modified monosaccharides.

As used herein, the term "multifunctional crosslinking agent" refers to a molecule having two or more reactive groups, such as electrophilic groups, capable of reacting with, for example, amino, hydroxy and/or alkoxy groups to form a covalent bond.

As used herein, the term "ionic polysaccharides" refers to both anionic and cationic polysaccharides.

As used herein, the term "fibers" refers to both natural and synthetic fibers.

The present invention relates to guanidinated polysaccharides. Surprisingly, it was discovered that guanidinated polysaccharides of Formula I:

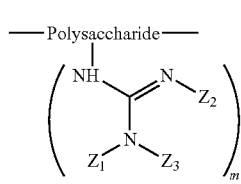

Formula I wherein Z$_1$, Z$_2$, Z$_3$ and m are as previously defined are particularly useful as absorbent materials.

In an embodiment of the present invention, the absorption capacities of the guanidinated polysaccharides are improved by converting the guanidinated polysaccharides into their corresponding highly absorbent cationic guanidinium salts. Because of their strongly alkaline nature, the guanidine groups can be readily converted into their corresponding more skin friendly cationic salts (i.e. pH ranging from 5 to 9). In an embodiment of the present invention, the guanidine groups are treated with acids such as monovalent acids. Non-limitative examples of monovalent acids include hydrochloric acid, hydrobromic acid, hydroiodic acid, monovalent organic acids such as acetic acid and propionic acid, as well as nitric acid.

Due to their strongly alkaline nature, the guanidinated polysaccharides of the present invention bear a cationic charge at neutral pH. The presence of the guanidinium ions results in increased absorption because guanidine is more strongly solvated when converted into its corresponding guanidinium salt, as a result of strong ion-dipole interactions.

Furthermore, the guanidinium ions affixed to the polysaccharides repel each other (i.e. coulombic interactions) and tend to stiffen the polysaccharide chains, resulting in larger occupied volumes (Buchholz F; Graham A; *Modern Superabsorbent technology*, Wiley-VCH, 1998, New-York, pp. 10).

The cationic guanidinium polysaccharides of the present invention are excellent superabsorbent materials, useful in many industrial applications such as in personal hygiene products including baby diapers, incontinence products, and sanitary napkins as well as in several other applications such as in the pulp and paper industry (i.e. absorbent paper products), in the textile industry, in printing applications, in ore treatments, in pet litter, in water treatment, in food pads (i.e. applications related to the transportation of fresh food and food packaging), in detergents, in oil drilling fluids (i.e. as lost circulation material), in agricultural and forestry applications for retaining water in the soil and for the release of water to the roots of plants and trees, in fire-fighting gels, in sealing materials, in anti-condensation coatings, in bandages and surgical pads (i.e. wound dressings), for the cleanup of acidic and/or basic aqueous spills including water soluble chemical spills, as polymeric gels for the slow and controlled release of cosmetics and pharmaceuticals (also known as drug delivery systems), as airlaids, and finally in the manufacture of artificial snow. Moreover, the cationic guanidinium polysaccharides of the present invention are useful in complexation chemistry, where they can be used to bind negatively charged species (i.e. particles, molecules).

The cationic guanidinium polysaccharides of the present invention have a high affinity for water, resulting in the likely partial solubilization of the polysaccharides.

The present invention also relates to water-swellable, water insoluble cationic guanidinium polysaccharides, obtained by cross-linking. A cross-linked guanidinium polysaccharide salt can be used to absorb and retain body fluids. Over-crosslinking will result in materials having reduced absorption characteristics.

In an embodiment of the present invention, the cationic guanidinium polysaccharides are crosslinked. Crosslinking provides stiffness to the gel, thus increasing its CRC and AUL properties. Furthermore, the water solubilization of the cationic guanidinium polysaccharides will also be reduced by crosslinking. However, as mentioned hereinabove, special precautions should be taken to avoid over cross-linking the cationic guanidinium polysaccharides. An over cross-linked cationic guanidinium polysaccharide will have reduced absorbent properties since the gel will be too stiff and unable to fully swell.

The cationic guanidinium polysaccharides of the present invention can be crosslinked by reacting the polysaccharides with one or more multifunctional crosslinking agents. In an embodiment of the present invention, crosslinking can occur via nucleophilic attack of the amino groups of the aminated polysaccharide on the electrophilic groups of the cross-linking agent (i.e. epichlorohydrin). This crosslinking results in the formation of a bridging unit linking two or more amino nitrogen atoms or alkoxy oxygen atoms, either from the same polymer strand or from different strands. In an embodiment of the present invention, the crosslinking reactions are carried out in alkaline solution. The crosslinking results in the formation of a gel-like material.

Non-limiting examples of multifunctional crosslinking agents as contemplated by the present invention include epihalohydrins, halohydrins, diacyl halides, bis-epoxy alkylenes, di-haloalkylenes, di-vinylsulfones, di-isocyanates, bis-acrylamides, trimetaphosphates, tripolyphosphates, phosphorous oxychloride, phosphoryl chloride, tetracarboxylic cyclic di-anhydrides (such as pyromellitic dianhydride or 1,2,3,4-butane-tetracarboxylic dianhydride), tricarboxylic cyclic anhydrides (such as citric anhydride or aconitic anhydride), dialdehydes, bis epoxy alkylene glycols, and bis halogenated alkylene glycols.

In contrast to their anionic counterparts, cationic polymers are less affected by the presence of multivalent cations as commonly encountered in physiological fluids and sea water, as well as in a variety of applications such as oil drilling and pulp and paper processes. Multivalent cations have the propensity to cause over-crosslinking of anionic superabsorbents, greatly limiting their use as absorbent materials.

Guanidinated polysaccharides can be obtained by grafting amidine groups to aminated polysaccharides. Non-limitative examples of aminated polysaccharides as contemplated by the present invention include naturally aminated polysaccharides such as chitosan, in addition to synthetically aminated polysaccharides obtained by O-alkylation reactions such as those described by Tassett (U.S. Pat. No. 4,464,528), Jarowenko et al. (U.S. Pat. No. 4,281,109), Harding et al. (U.S. Pat. No. 4,505,775), Caesar (U.S. Pat. No. 3,422,087) and Schlack (U.S. Pat. No. 2,131,120). Moreover, guanidinated polysaccharides can also be obtained by the derivatization of cellulose, starch, amylopectin, amylose, chitosan, chitin, guar gum, locust bean gum, tara gum, konjac, fenugreek gum, mesquite gum, aloe mannans, pectin, arabic gum, karaya gum, xanthan, kappa, iota or lambda carrageenans, agar-agar, and alginates.

In an embodiment of the present invention, the absorbent guanidinated polysaccharides and the cationic guanidinated polysaccharides are in a dry state. These dry polysaccharides can be easily handled and stocked. Dry powders of the cationic guanidinated polysaccharides can be obtained by precipitating the polysaccharides using hydrophilic organic solvents. Non-limitative examples of hydrophilic organic solvents as contemplated by the present invention include $C_1$-$C_3$ alcohols, acetone, acetonitrile and ethylene glycol. In an embodiment of the present invention, the cationic guanidinated polysaccharides are precipitated using methanol.

The guanidinated polysaccharides of the present invention can be readily mixed with other co-absorbent materials. Non-limitative examples of co-absorbent materials as contemplated by the present invention include cellulose fibers, synthetic absorbents or even other polysaccharides. In an embodiment of the present invention, the guanidinated polysaccharides are in a particulate state. In a further embodiment of the present invention, the particulate guanidinated polysaccharides have a particle size ranging from about 80 μm to about 580 μm. The guanidinated polysaccharides, when in particulate form, facilitate the mixing process.

In an embodiment of the present invention, the cationic guanidinated polysaccharides are mixed with other co-absorbent materials to provide superabsorbent compositions. In an embodiment of the present invention, the superabsorbent compositions comprise from about 1 to about 99% (w/w) of a guanidinium polysaccharide salt and from about 99 to about 1% (w/w) of a co-absorbent material. Non-limitative co-absorbent materials as contemplated by the present invention include synthetic superabsorbent polymers, mannose-based polysaccharides, ionic polysaccharides, fibers and mixtures thereof. In a further embodiment of the present invention, superabsorbent compositions are obtained by mixing the cationic guanidinated polysaccharides with both cationic and anionic polysaccharides. In yet a further embodiment of the present invention, superabsorbent compositions are obtained by mixing the cationic guanidinated polysaccharides with one or more anionic polysaccharides.

The synthetic superabsorbent polymers to be used as co-absorbent materials in the absorbent compositions of the present invention, are generally obtained from the polymerization of monomers, non-limitative examples of which include acrylic acid, acrylate salts, acrylic ester, acrylic anhydride, methacrylic acid, methacrylate salts, methacrylic esters, methacrylic anhydride, maleic anhydride, maleic salts, maleate esters, acrylamide, acrylonitrile, vinyl alcohol, vinyl pyrrolidone, vinyl acetate, vinyl guanidine, aspartic acid, aspartic salts and mixtures thereof. In an embodiment of the present invention, the synthetic superabsorbent polymers are obtained by radical or radical graft polymerization.

Non-limitative examples of mannose-based polysaccharides as contemplated by the present invention include guar gum, tara gum, locust bean gum, konjac, mesquite gum, fenugreek extracts and mixtures thereof.

Non-limitative examples of anionic polysaccharides as contemplated by the present invention include carboxyalkyl polysaccharides, carboxymethyl cellulose, carboxymethyl starch, oxidized polysaccharides, xanthan, carrageenans, pectin and mixtures thereof.

Non-limitative examples of cationic polysaccharides as contemplated by the present invention include cationic starch, chitosan salts, cationic galactomannans and cationic cellulose.

Non-limitative examples of fibers as contemplated by the present invention include cellulose, viscose, rayon, cellulose acetate, Nylon™, polyalkylenes, polyethylene, polypropylene, bi-component fibers, polyesters, polylactides, polypropanediols, Lyocell™, sphagnum and mixtures thereof.

The superabsorbent cationic guanidinated polysaccharides of the present invention are characterized by their Free Swell Capacity (FSC), their Centrifuge Retention Capacity (CRC) and their Absorption Under Load (AUL) capacity, at 0.3 PSI (2.06 KPa). The FSC and CRC are standard tests in the field of superabsorbents, used for all applications related to personal hygiene. The AUL capacity is a standard test for baby diapers.

The guanidinated polysaccharides of the present invention are used in methods for absorbing liquids. In an embodiment of the present invention, one or more of the guanidinated polysaccharides are contacted with a liquid to be absorbed. Non-limitative examples of liquids as contemplated by the present invention include water, aqueous solutions, physiological solutions and saline solutions. The guanidinated polysaccharides, upon contact with the liquid(s) to be absorbed, will form a gel trapping the liquid(s) within.

The guanidinated polysaccharides of the present invention are used in methods for absorbing liquids comprising at least one active ingredient to form a hydrogel. Such hydrogels can be used for the delayed and/or sustained release of the active ingredient(s) in various applications, non-limitative examples of which are wound dressings, drug delivery, and implants.

The synthesis of polymers bearing guanidinium groups as bile sequestrants has been previously disclosed by Dhal et al. (U.S. Pat. No. 6,294,163). More specifically, Dhal et al. report on the reaction of a polyamine with a guanylating agent (1-H-pyrazole-1-carboxamidine.HCl).

Surprisingly, it was discovered that aminated polysaccharides can be made to react with guanylating agents comprising a good leaving group, to provide guanidinated polysaccharides, as shown below in Scheme 1.

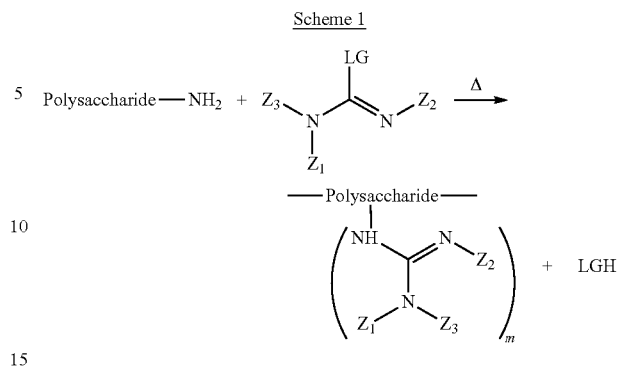

Non-limitative examples of suitable leaving groups as contemplated by the present invention include, but are not limited to, pyrazoles, chlorides, bromides, iodides, cyanides, azides, thiocyanates, tosylates, mesylates, triflates, picrates, nosylates and brosylates. In an embodiment of the present invention, the leaving group is a pyrazole.

The amount of guanidinating agent used, will depend on the desired type of absorbent polysaccharide. Typical amounts of guanidinating agent used will range from about 1% to about 100% relative to the number of reactive groups present on the polysaccharide.

In an embodiment of the present invention, and as illustrated below in Scheme 2, a 1-H-pyrazole-1-carboxamidine derivative is reacted with an aminated polysaccharide to provide a guanidinated polysaccharide in moderate to high yields (yields ranging from about (85-90%). The guanidinating agent 1-H-pyrazole-1-carboxamidine readily reacts with the aminated polysaccharide with the concomitant liberation of 1-pyrazolyl, a good leaving group capable of stabilizing the nascent negative charge.

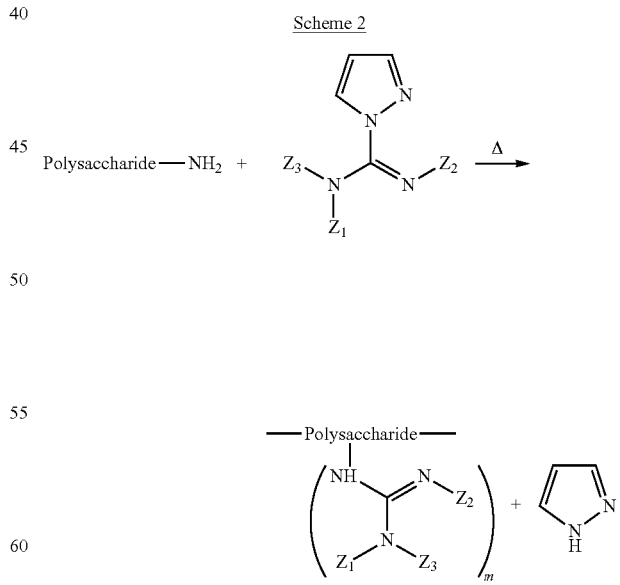

Furthermore, as illustrated below in Scheme 3, it was discovered that guanidinated polysaccharides can also be obtained by reacting an aminated polysaccharide with a carbodiimide derivative ($Z_1$—N=C=N-$Z_2$).

Scheme 3

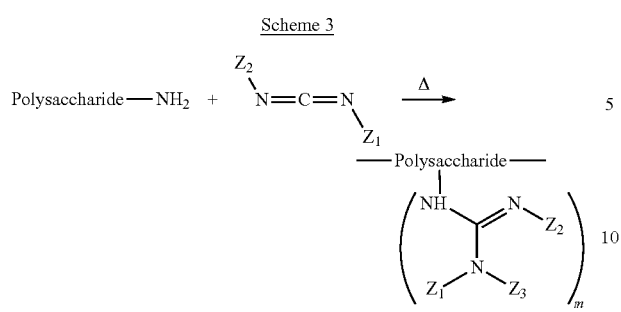

The $Z_1$ and $Z_2$ substituents of the carbodiimide derivative are independently selected from the group consisting of hydrogen, $C_1$-$C_{10}$ alkyl, substituted $C_1$-$C_{10}$ alkyl, $C_5$-$C_7$ cyclically and benzyl, wherein the substituents are selected from the group consisting of $C_1$-$C_5$ alkyl, and amino groups. In an embodiment of the present invention, the $Z_1$ and $Z_2$ substituents are independently selected from the group consisting of ethyl, substituted propyl, and cyclohexyl. In yet a further embodiment of the present invention, the carbodiimide derivative is selected from the group consisting of N-ethyl-N'-(3-dimethylaminopropyl)carbodiimide (EDC) and dicyclohexylcarbodiimide (DCC).

For the guanylation reactions to occur, the polyamine (e.g. chitosan, aminated polysaccharide) must be in its free amino form (i.e. non-salt form). It is to be understood that any additive capable of neutralizing a chitosan solution, and which is also capable of maintaining the chitosan or the aminated polymer in its free-amino form without precipitating the chitosan or the aminated polysaccharide, is within the scope of the present invention. Non-limitative examples of additives include N-hydroxysuccinimide (NHS) and derivatives thereof, as well as 2,2'-Bis(hydroxymethyl)-2,2',2''-nitrilotriethanol (Bis-Tris).

Methods and Materials

Chitosan Chitoclear FGlv [Deacetylation degree (D.A.D.): 85%; Molecular weight: $3 \times 10^5$ Da.] was obtained from Primex ehf, (Siglufjordur, Iceland) (Lot TM1264). Chitosan Chitoclear FGlv was extracted from shrimp shells. Chitosan flakes were dissolved in aqueous hydrochloric acid (0.1N) and precipitated with aqueous NaOH (2N). The precipitated chitosan was washed several times with water and vacuum dried in a dessicator.

Methanol, sodium hydroxide and concentrated hydrochloric acid were obtained from Laboratoire MAT (Beauport, Canada).

Research grade glacial acetic acid, pyridine, N-ethyl-N'-(3-dimethylaminopropyl)carbodiimide hydrochloride (EDC), 1-H-pyrazole-1-carboxamidine, dicyclohexylcarbodiimide (DCC), N-hydroxysuccinimide (NHS) and 2,2'-Bis(hydroxymethyl)-2,2',2''-nitrilotriethanol (Bis-Tris), were obtained from Sigma-Aldrich Chemicals (Saint-Louis, USA).

AUL measurements: the Absorption Under Load (AUL) in a 0.9% NaCl solution at 0.3 PSI, was determined according to the recommended test method 442.2-02 from EDANA, using 0.1 gram of the absorbent in the apparatus.

FSC and CRC measurements were carried out using tea bags (10×10 cm), prepared from heat sealable Ahistrom filter paper (16.5±0.5) g/m².

FSC measurements: the Free Swell Capacity (FSC) in a 0.9% NaCl solution was determined according to the recommended test method 440.2-02 from EDANA.

CRC measurements: the Centrifuge Retention Capacity (CRC) in a 0.9% NaCl solution was determined according to the recommended test method 441.2-02 from EDANA.

Composition percentages: Composition percentages are all related in weight by weight (w/w) percentages.

The invention will now be further illustrated by the following non-limitative examples:

EXAMPLE 1

Preparation of a Chitosan Guanidine Using EDC

Chitosan was purified from residual proteins and inorganic impurities by dissolution in 0.1M acetic acid, followed by precipitation in 0.1M sodium hydroxide and extensive washing of the precipitate with deionized distilled water. The dissolution-precipitation-washing process was repeated twice.

One gram of chitosan was dissolved in 0.1M acetic acid (100 mL). A cooled aqueous solution of Bis-Tris (10 mL) was slowly added under continuous stirring. When the pH of the transparent homogeneous chitosan solution reached values ranging from about 6.3-7.1, without precipitation of the chitosan, an aqueous EDC solution (1 g per mL of water) was slowly added. The final concentration of EDC in the reaction medium was controlled to provide for different guanidine:amine ratios. The reaction between the carbodiimide group of EDC and the primary amine group of the D-glucosamine residue of chitosan was allowed to proceed for 1 h at room temperature, or, alternatively, for a period ranging from 1 to 30 minutes at temperatures ranging from 37-45° C., while in the presence of a catalytic amount (1%) of NHS (1 g per ml of water). The NHS can be added prior to, or following the addition of EDC. Transparent and strong hydrogels were obtained. The gels were washed extensively with deionized distilled water until complete removal of any unreacted EDC. The modified chitosan was then isolated by alcohol precipitation techniques. The substitution efficiency was found to be dependent on the degree of deacetylation of chitosan. Typical reaction yields were of the order of 85-95%. The FSC and CRC values for the resulting guanidinated product were measured to be of the order of 8 g/g and 3.17 g/g respectively.

EXAMPLE 2

Preparation of a Chitosan Guanidine Using DCC

Chitosan solutions (1.7% w/w) were prepared using hydrochloric acid (0.1M) at room temperature. Chitosan powder was progressively added to the solvent while stirring, and mixing was continued for an additional 3 hrs. A chilled 8% (w/w) Bis-Tris aqueous solution was then carefully added drop wise, to provide clear, homogeneous solutions. The solutions were mixed for an additional 10 minutes at 4° C. The pH of the final cold solutions ranged from about 6.9 to 7.2. A transparent hydrogel was finally obtained following the addition of DCC (1 eq.), and heating at 37° C. for 30 minutes.

EXAMPLE 3

Preparation of an Epichlorohydrin Cross-Linked Guanidinated Chitosan Hydrochloride obtained using 1-H-Pyrazole 1-Carboxamidine Chitosan (4.3 g) was suspended in deionized water (125 mL). After stirring for 30 minutes, a deionized water solution (60 mL) containing 1-H-pyrazole-1-carboxamidine.HCl (Aldrich; 7.3 g) and potassium carbonate (7.0 g) was added to the polymer suspension. The reaction mixture was then stirred at room temperature for 3 hours, and subsequently for an additional 14 hours at 60° C. After cooling to room temperature, the reaction mixture was filtered and the residue washed with deionized water (300 mL). The polymer particles were suspended in deionized water (250 mL), stirred for 30 minutes, and filtered. This process was repeated three more times. The polymer was subsequently dispersed in deionized water (100 mL), followed by the addition of concentrated HCl (2 mL). After stirring for 30 minutes, the slurry was filtered, and the isolated solid dried at 60° C. to provide the desired polymer as an off-white solid (5 g).

The polymer (4 g) was suspended in deionized water (80 mL) followed by the addition of NaOH (3.3 mL; 30%), and stirring for 2 hours. Epichlorohydrin (0.9 mL) was then added to the polymer solution while stirring. The polymer solution was then stirred at 60° C. for 18 hours. The obtained cross-linked polymer was suspended in deionized water (500 mL), stirred for 30 minutes, and filtered. This washing process was repeated two more times, followed by the addition of concentrated HCl (4 mL). After stirring for 30 minutes, the slurry was filtered and the isolated solid dried at 60° C., yielding the desired cross-linked polymer as an off-white solid (3.5 g). The Free Swell Capacity (FSC), Centrifuge Retention Capacity (CRC) and Absorption Under Load (AUL) were then measured to be of the order of 29.0 g/g, 24.0 g/g and 20.0 g/g respectively.

EXAMPLE 4

Preparation of a Glyoxal Cross-Linked Guanidinated Chitosan Obtained using 1-H-Pyrazole-1-Carboxamidine Chitosan (2.15 g), was suspended in deionized water (62.5 mL). After stirring for 30 minutes, a deionized water solution (30 mL) containing 1-H-pyrazole-1-carboxamidine.HCl (10.95 g) and potassium carbonate (10.50 g) was added to the polymer suspension. The reaction mixture was then stirred at 70° C. for 14 hours. After cooling to room temperature, the reaction mixture was filtered and the residue washed three times with deionized water (300 mL).

The polymer particles were suspended in deionized water (80 mL), followed by the addition of concentrated HCl (2 mL). After stirring for 5 minutes, a glyoxal solution (5%) was added (81.60 mL). The resulting slurry was stirred for 45 minutes, and then centrifuged to remove the acid solution. The obtained gel was precipitated in sodium hydroxide (450 mL, 0.2 N), resulting in a slurry which was stirred for 3 days. The slurry was filtered and dried at room temperature, yielding the desired cross-linked polymer as a white flaky solid. The product was characterized by a neat N—C=N infrared band, observed at 1656 cm$^{-1}$. The Free Swell Capacity (FSC) of the product was measured to be 19.0 g/g.

It is to be understood that the invention is not limited in its application to the details of construction and parts as described hereinabove. The invention is capable of other embodiments and of being practiced in various ways. It is also understood that the phraseology or terminology used herein is for the purpose of description and not limitation. Hence, although the present invention has been described hereinabove by way of illustrative embodiments thereof, it can be modified, without departing from the spirit, scope and nature of the subject invention as defined in the appended claims.

What is claimed is:

1. An absorbent guanidinated polysaccharide of Formula I:

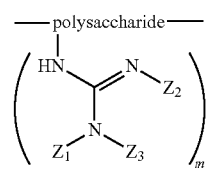

Formula I wherein:
Z$_1$, Z$_2$ and Z$_3$ are independently selected from the group consisting of hydrogen, C$_1$-C$_{10}$ alkyl, substituted C$_1$-C$_{10}$ alkyl, C$_5$-C$_7$ cycloalkyl, and benzyl; and
m is an integer ranging from 1 to 2,000,000, wherein the absorbent guanidinated polysaccharide is in the form of a powder.

2. The absorbent guanidinated polysaccharide of claim 1, wherein the at least one of Z$_1$,Z$_2$ and Z$_3$ is selected from the group consisting of C$_1$-C$_5$ alkyl and C$_1$-C$_5$ alkyl amino groups.

3. The absorbent guanidinated polysaccharide of claim 1, wherein the polysaccharide further comprises guanidinium ions.

4. The absorbent guanidinated polysaccharide of claim 3, wherein the guanidinium ions are acid addition salts of guanidine.

5. The absorbent guanidinated polysaccharide of claim 4, wherein the acid is selected from the group consisting of hydrochloric acid, hydrobromic acid, hydroiodic acid, and monovalent organic acids.

6. The absorbent guanidinated polysaccharide of claim 5, wherein the monovalent organic acids are selected from the group consisting of acetic acid, propionic acid, and nitric acid.

7. The absorbent guanidinated polysaccharide of claim 1, wherein the guanidinated polysaccharide is obtained using an aminated polysaccharide.

8. The absorbent guanidinated polysaccharide of claim 7, wherein the aminated polysaccharide is selected from the group consisting of chitosan and synthetically aminated polysaccharides.

9. The absorbent guanidinated polysaccharide of claim 8, wherein the synthetically aminated polysaccharides are obtained by amination of a polysaccharide selected from the group consisting of cellulose, starch, amylopectin, amylose, chitosan, chitin, guar gum, locust bean gum, tara gum, konjac gum, fenugreek gum, mesquite gum, aloe mannans, pectin, arabic gum, karaya gum, xanthan, kappa, iota or lambda carrageenans, agar-agar, and alginates.

10. The absorbent guanidinated polysaccharide of claim 1, wherein the guanidinated polysaccharide is crosslinked.

11. The absorbent guanidinated polysaccharide of claim 10, wherein the guanidinated polysaccharide is cross-linked with a crosslinking agent selected from the group consisting of epihalohydrins, halohydrins, diacyl halides, bis-epoxy alkylenes, di-haloalkylenes, divinylsulfones, di-isocyanates, bis-acrylamides, trimetaphosphates, tripolyphosphates, phosphorous oxychloride, phosphoryl chloride, tetracarboxylic cyclic di-anhydrides pyromellitic dianhydride, 1,2,3, 4-butane-tetracarboxylic dianhydride, tricarboxylic cyclic anhydrides citric anhydride, aconitic anhydride, dialdehydes, bis epoxy alkylene glycols, and bis halogenated alkylene glycols.

12. The absorbent guanidinated polysaccharide of claim 11 wherein the powder is a particulate material comprising a particle size ranging from about 80 μm to about 580 μm.

13. A method for absorbing liquids comprising contacting a liquid with an absorbent guanidinated polysaccharide of claim 12.

14. The method of claim 13, wherein the liquids are selected from the group consisting of water, aqueous solutions, physiological fluids and saline solutions.

15. The absorbent guanidinated polysaccharide of claim 12 wherein the absorbent material is comprised in products selected from the group consisting of diapers, incontinence products, airlaids, feminine hygiene products, absorbent dressings, sealing materials, anti-condensation coatings, fire-fighting gels, water-storing materials, absorbent paper products, surgical absorbents, pet litter, bandages, wound dressings, surgical drapes, artificial snow, chemical absorbents and food pads.

16. An absorbent composition comprising an absorbent guanidinated polysaccharide as defined in claim 1 and at least one co-absorbent material.

17. The absorbent composition as defined in claim 16, wherein the co-absorbent material is selected from the group consisting of synthetic superabsorbent polymers, mannose-based polysaccharides, ionic polysaccharides, fibers and mixtures thereof.

18. The absorbent composition as defined in claim 17, wherein the synthetic superabsorbent polymers are obtained by the polymerization of monomers selected from the group consisting of acrylic acid, acrylate salts, acrylic ester, acrylic anhydride, methacrylic acid, methacrylate salts, methacrylic esters, methacrylic anhydride, maleic anhydride, maleic salts, maleate esters, acrylamide, acrylonitrile, vinyl alcohol, vinyl pyrrolidone, vinyl acetate, vinyl guanidine, aspartic acid, aspartic salts and mixtures thereof.

19. The absorbent composition as defined in claim 17, wherein the mannose-based polysaccharides are selected from the group consisting of guar gum, tara gum, locust bean gum, konjac, mesquite gum, fenugreek extracts and mixtures thereof.

20. The absorbent composition as defined in claim 17, wherein the ionic polysaccharides comprise anionic and cationic polysaccharides.

21. The absorbent composition as defined in claim 20, wherein the anionic polysaccharides are selected from the group consisting of carboxyalkyl polysaccharides, carboxymethyl cellulose, carboxymethyl starch, oxidized polysaccharides, xanthan, carrageenans, pectin and mixtures thereof.

22. The absorbent composition as defined in claim 20, wherein the cationic polysaccharides are selected from the group consisting of cationic starch, chitosan salts, cationic galactomannans and cationic cellulose.

23. The absorbent composition as defined in claim 17, wherein the fibers are selected form the group consisting of cellulose, viscose, rayon, cellulose acetate, nylon cellulose fiber sold under the tradename Lyocell, polyalkylenes, polyethylene, polypropylene, bi-component fibers, polyesters, polylactides, polypropanediols, Lyocell cellulose fiber sold under the tradename Lyocell, sphagnum and mixtures thereof.

24. A process for producing a guanidinated polysaccharide as defined in claim 1 comprising reacting an aminated polysaccharide of Formula II:

Polysaccharide-NH$_2$  Formula II with a compound of Formula III:

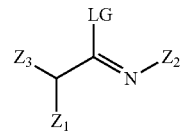

Formula III wherein
$Z_1$, $Z_2$ and $Z_3$ are independently selected from the group consisting of hydrogen, $C_1$-$C_{10}$ alkyl, substituted $C_1$-$C_{10}$ alkyl, $C_5$-$C_7$ cycloalkyl, and benzyl; and
LG is a leaving group selected from the group consisting of pyrazoles, chlorides, bromides, iodides, cyanides, azides, thiocyanates, tosylates, mesylates, triflates, picrates, nosylates and brosylates.

25. A process for producing a guanidinated polysaccharide as defined in claim 1 comprising reaction an aminated polysaccharide of Formula II:

Polysaccharide-NH$_2$  Formula II with a compound of Formula IV:

$Z_1$—N=C=N—$Z_2$  Formula IV wherein
$Z_1$ and $Z_2$ are independently selected from the group consisting of hydrogen, $C_1$-$C_{10}$ alkyl, substituted $C_1$-$C_{10}$ alkyl, $C_5$-$C_7$ cycloalkyl, and benzyl.

26. The process of claim 24, wherein the leaving group is a pyrazole.

27. The process of claim 24 wherein the aminated polysaccharide is selected from the group consisting of chitosan and synthetically aminated polysaccharides.

28. The process of claim 27, wherein the synthetically aminated polysaccharides are obtained by amination of a polysaccharide selected from the group consisting of cellulose, starch, amylopectin, amylose, chitosan, chitin, guar gum, locust bean gum, tara gum, konjac gum, fenugreek gum, mesquite gum, aloe mannans, pectin, arabic gum, karaya gum, xanthan, kappa, iota or lambda carrageenans, agar-agar, and alginates.

29. The process of claim 24 wherein the guanidinated polysaccharide is cross-linked.

30. The process of claim 29, wherein the guanidinated polysaccharide is cross-linked with a crosslinking agent selected from the group consisting of epihalohydrins, halohydrins, diacyl halides, bis-epoxy alkylenes, di-haloalkylenes, di-vinylsulfones, di-isocyanates, bisacrylamides, trimetaphosphates, tripolyphosphates, phosphorous oxychloride, phosphoryl chloride, tetracarboxylic cyclic dianhydrides (such as pyromellitic dianhydride or 1,2,3,4-butane-tetracarboxylic dianhydride), tricarboxylic cyclic anhydrides (such as citric anhydride or aconitic anhydride), dialdehydes, bis epoxy alkylene glycols, and bis halogenated alkylene glycols.

31. The process of claim 24 wherein the guanidinated polysaccharide is treated with an acid selected from the group consisting of hydrochloric acid, hydrobromic acid, hydroiodic acid, and monovalent organic acids, resulting in a cationic guanidinated polysaccharide.

32. The process of claim 31, wherein the monovalent organic acids are selected from the group consisting of acetic acid, propionic acid, and nitric acid.

33. The process of claim 25 wherein the aminated polysaccharide is selected from the group consisting of chitosan and synthetically aminated polysaccharides.

34. The process of claim 33, wherein the synthetically aminated polysaccharides are obtained by amination of a polysaccharide selected from the group consisting of cellulose, starch, amylopectin, amylose, chitosan, chitin, guar gum, locust bean gum, tara gum, konjac gum, fenugreek gum, mesquite gum, aloe mannans, pectin, arabic gum, karaya gum, xanthan, kappa, iota or lambda carrageenans, agar-agar, and alginates.

35. The process of claim 25 wherein the guanidinated polysaccharide is cross-linked.

36. The process of claim 35, wherein the guanidinated polysaccharide is cross-linked with a crosslinking agent selected from the group consisting of epihalohydrins, halohydrins, diacyl halides, bis-epoxy alkylenes, di-haloalkylenes, di-vinylsulfones, di-isocyanates, bisacrylamides, trimetaphosphates, tripolyphosphates, phosphorous oxychloride, phosphoryl chloride, tetracarboxylic cyclic dianhydrides (such as pyromellitic dianhydride or 1,2,3,4-butane-tetracarboxylic dianhydride), tricarboxylic cyclic anhydrides (such as citric anhydride or aconitic anhydride), dialdehydes, bis epoxy alkylene glycols, and bis halogenated alkylene glycols.

37. The process of claim 25 wherein the guanidinated polysaccharide is treated with an acid selected from the group consisting of hydrochloric acid, hydrobromic acid, hydroiodic acid, and monovalent organic acids, resulting in a cationic guanidinated polysaccharide.

38. The process of claim 37, wherein the monovalent organic acids are selected from the group consisting of acetic acid, propionic acid, and nitric acid.

39. An absorbent guanidinated polysaccharide of Formula I:

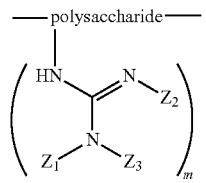

Formula I wherein:
  $Z_1$, $Z_2$ and $Z_3$ are independently selected from the group consisting of hydrogen, $C_1$-$C_{10}$ alkyl, substituted $C_1$-$C_{10}$ alkyl, $C_5$-$C_7$ cycloalkyl, and benzyl; and
  m is an integer ranging from 1 to 2,000,000, wherein the absorbent guanidinated polysaccharide is in the form of a powder; and
  the guanidinated polysaccharide is cross-linked with a multifunctional cross-linking agent.

* * * * *